(12) United States Patent
Matsumoto et al.

(10) Patent No.: US 6,225,474 B1
(45) Date of Patent: May 1, 2001

(54) POLYMORPHS OF 2-(3-CYANO-4-ISOBUTYLOXYPHENYL)-4-METHYL-5-THIAZOLECARBOXYLIC ACID AND METHOD OF PRODUCING THE SAME

(75) Inventors: Koichi Matsumoto; Kenzo Watanabe; Toshiyuki Hiramatsu, all of Iwakuni; Mitsutaka Kitamura, Higashi-Hiroshima, all of (JP)

(73) Assignee: Teijin Limited, Osaka (JP)

( * ) Notice: Subject to any disclaimer, the term of this patent is extended or adjusted under 35 U.S.C. 154(b) by 0 days.

(21) Appl. No.: 09/485,861

(22) PCT Filed: Jun. 18, 1999

(86) PCT No.: PCT/JP99/03258

§ 371 Date: Feb. 17, 2000

§ 102(e) Date: Feb. 17, 2000

(87) PCT Pub. No.: WO99/65885

PCT Pub. Date: Dec. 23, 1999

(30) Foreign Application Priority Data

Jun. 19, 1998 (JP) .................................. 10-173079

(51) Int. Cl.$^7$ ................................ C07C 277/18
(52) U.S. Cl. ............................................ 548/201
(58) Field of Search .............................. 514/305; 548/201

(56) References Cited

U.S. PATENT DOCUMENTS 5,614,520 3/1997 Kondo et al. ...................... 514/236.8

FOREIGN PATENT DOCUMENTS

| 6-345724 | 12/1994 | (JP) | ............................. C07C/327/48 |
| 10-45733 | 2/1998 | (JP) | ............................. C07D/277/56 |
| 92/09279 | 6/1992 | (WO) | ........................... A61K/31/425 |

Primary Examiner—James H. Reamer
(74) Attorney, Agent, or Firm—Sughrue, Mion, Zinn, Macpeak & Seas, PLLC

(57) ABSTRACT

The present invention provides a technique of selectively producing a desired polymorph of 2-(3-cyano-4-isobutyloxyphenyl)-4-methyl-5-thiazolecarboxylic acid.

The present invention also provides a method of producing various polymorphs of 2-(3-cyano-4-isobutyloxyphenyl)-4-methyl-5-thiazolecarboxylic acid, which comprises crystallizing under the conditions defined by a specific temperature and a composition of a mixed solvent of methanol and water, and polymorphs obtained by the method.

The present invention further provides a method of producing the other polymorphs or amorphous compounds by drying a specific polymorph under a reduced pressure with heating, and the other polymorphs or amorphous compounds obtained by the method.

27 Claims, 12 Drawing Sheets

POLYMORPHS OF 2-(3-CYANO-4-ISOBUTYLOXYPHENYL)-4-METHYL-5-THIAZOLECARBOXYLIC ACID AND METHOD OF PRODUCING THE SAME

TECHNICAL FIELD

The present invention relates to a technique for controlling polymorphs, which is important in the case where a pharmaceutical composition comprising a useful compound as a drug is supplied in a qualitatively stable manner. More particularly, it relates to a method of producing a polymorph of 2-(3-cyano-4-isobutyloxyphenyl)-4-methyl-5-thiazolecarboxylic acid. This compound has an activity to regulate biosynthesis of uric acid in vivo and can be used as a therapeutic agent for hyperuricemia.

BACKGROUND ART

When a certain compound forms two or more crystalline states, these different crystalline states are referred to as polymorphism. It is generally known that the stability varies with each polymorph (crystal form) of polymorphism. For example, Japanese Unexamined Patent Publication (KOKAI) No. 62-226980 describes that two polymorphs of prazosin hydrochloride each having a different stability, thus exerting an influence on the results of the long-term storage stability. Also, Japanese Unexamined Patent Publication (KOKAI) No. 64-71816 describes that a specific one among different polymorphs of buspirone hydrochloride is advantageous in view of retention of specific physical properties under storage or manufacturing conditions.

As described above, a specific polymorph is superior in stability, sometimes. Accordingly, in case where a plurality of polymorphs are present, it is important to develop a technique of preferentially producing each polymorph. Particularly, in case where a pharmaceutical composition comprising a useful compound as a drug is produced, it is suitable to control polymorphism so as to formulate a pharmaceutical composition containing only a superior specific polymorph.

As described in International Publication WO92/09279, it is known that 2-(3-cyano-4-isobutyloxyphenyl)-4-methyl-5-thiazolecarboxylic acid represented by the following formula has an activity for inhibiting xanthine oxidase.

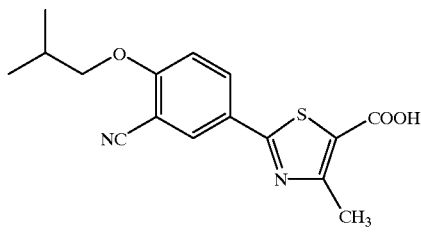

However, the above-mentioned publication does not describe polymorphism, and therefore, the crystal form of 2-(3-cyano-4-isobutyloxyphenyl)-4-methyl-5-thiazolecarboxylic acid studied in the publication is not clear. It is only assumed from the experimental operation described therein that it is an ethanolate. The evaluation of the activity described in that publication is not conducted in a solid state and, therefore, there is not any description about characteristics of the polymorph.

Polymorphism is meaningless unless solid physical properties exert an influence on biological activity, physiochemical properties or an industrial manufacturing method of the substance. For example, when using as a solid preparation in animals, it is important that the presence or absence of polymorphism is confirmed in advance and a technique of selectively producing a desired polymorph is developed. In case where the substance is stored for a long period of time, a question is how the crystal form can be retained in a stable manner. It is also an important object to develop a technique of producing the crystal form in an industrially easy and reproducible manner.

DISCLOSURE OF THE INVENTION

Accordingly, an object of the present invention is to solve the above-described problems about 2-(3-cyano-4-isobutyloxyphenyl)-4-methyl-5-thiazolecarboxylic acid. That is, the present invention provides a technique of selectively producing desired various polymorphs if polymorphism is present after confirming the presence or absence of polymorphism.

The present inventors have intensively studied, and found that at least six polymorphs including an amorphous compound and a solvate are present for 2-(3-cyano-4-isobutyloxyphenyl)-4-methyl-5-thiazolecarboxylic acid. It has been found that the solvate includes two members (methanolate and hydrate). It has also been found that all polymorphs other than the amorphous compound exhibit characteristic X-ray powder diffraction (XRD) patterns. Each polymorph has a specific $2\theta$ value. Even in case where two or more polymorphs are present simultaneously, the content of about 0.5% can be detected by X-ray powder diffraction analysis.

Each of all polymorphs including the amorphous compound exhibits a characteristic absorption pattern in infrared (IR) spectroscopic analysis. Furthermore, sometimes, each polymorph exhibits a different melting point. In this case, the polymorphism can also be analyzed by differential scanning calorimetry (DSC).

Also the present inventors have studied a method for producing those polymorphs and found a technique for obtaining 2-(3-cyano-4-isobutyloxyphenyl)-4-methyl-5-thiazolecarboxylic acid in the desired crystal form.

Thus, the present invention provides a polymorph of 2-(3-cyano-4-isobutyloxyphenyl)-4-methyl-5-thiazolecarboxylic acid (hereinafter also referred to as crystal A), which shows a X-ray powder diffraction pattern having characteristic peaks at a reflection angle $2\theta$ of about 6.62, 7.18, 12.80, 13.26, 16.48, 19.58, 21.92, 22.68, 25.84, 26.70, 29.16 and 36.70°;

a polymorph of 2-(3-cyano-4-isobutyloxyphenyl)-4-methyl-5-thiazolecarboxylic acid (hereinafter also referred to as crystal B), which shows a X-ray powder diffraction pattern having characteristic peaks at a reflection angle $2\theta$ of about 6.76, 8.08, 9.74, 11.50, 12.22, 13.56, 15.76, 16.20, 17.32, 19.38, 21.14, 21.56, 23.16, 24.78, 25.14, 25.72, 26.12, 26.68, 27.68 and 29.36°;

a polymorph of 2-(3-cyano-4-isobutyloxyphenyl)-4-methyl-5-thiazolecarboxylic acid (hereinafter also referred to as crystal C), which shows a X-ray powder diffraction pattern having characteristic peaks at a reflection angle $2\theta$ of about 6.62, 10.82, 13.36, 15.52, 16.74, 17.40, 18.00, 18.70, 20.16, 20.62, 21.90, 23.50, 24.78, 25.18, 34.08, 36.72 and 38.04°;

a polymorph of 2-(3-cyano-4-isobutyloxyphenyl)-4-methyl-5-thiazolecarboxylic acid (hereinafter also referred to as crystal D), which shows a X-ray powder diffraction pattern having characteristic peaks at a reflection angle 2θ of about 8.32, 9.68, 12.92, 16.06, 17.34, 19.38, 21.56, 24.06, 26.00, 30.06, 33.60 and 40.34°; and a polymorph of 2-(3-cyano-4-isobutyloxyphenyl)-4-methyl-5-thiazolecarboxylic acid (hereinafter also referred to as crystal G), which shows a X-ray powder diffraction pattern having characteristic peaks at a reflection angle 2θ of about 6.86, 8.36, 9.60, 11.76, 13.74, 14.60, 15.94, 16.74, 17.56, 20.00, 21.26, 23.72, 24.78. 25.14, 25.74, 26.06, 26.64, 27.92, 28.60, 29.66 and 29.98°.

According to infrared spectroscopic analysis, the crystal A has a characteristic absorption, which can be distinguished from that of other polymorphs, at about 1678 cm$^{-1}$; the crystal B has characteristic absorptions, which can be distinguished from the other polymorphs, at about 1715, 1701 and 1682 cm$^{-1}$; the crystal C has characteristic absorptions, which can be distinguished from the other polymorphs, at about 1703 and 1219 cm$^{-1}$; the crystal D has a characteristic absorption, which can be distinguished from that of other polymorph, at about 1705 cm$^{-1}$; and the crystal G has characteristic absorptions, which can be distinguished from the other polymorph, at about 1703 and 1684 cm$^{-1}$.

That is, the present invention provides a polymorph of 2-(3-cyano-4-isobutyloxyphenyl)-4-methyl-5-thiazolecarboxylic acid (crystal A) having a characteristic absorption, which can be distinguished from that of other polymorphs, at about 1678 cm$^{-1}$ in infrared spectroscopic analysis;

a polymorph of 2-(3-cyano-4-isobutyloxyphenyl)-4-methyl-5-thiazolecarboxylic acid (crystal B) having characteristic absorptions, which can be distinguished from that of other polymorphs, at about 1715, 1701 and 1682 cm$^{-1}$ in infrared spectroscopic analysis;

a polymorph of 2-(3-cyano-4-isobutyloxyphenyl)-4-methyl-5-thiazolecarboxylic acid (crystal C) having characteristic absorptions, which can be distinguished from that of other polymorphs, at about 1703 and 1219 cm$^{-1}$ in infrared spectroscopic analysis;

a polymorph of 2-(3-cyano-4-isobutyloxyphenyl)-4-methyl-5-thiazolecarboxylic acid (crystal D) having a characteristic absorption, which can be distinguished from that of other polymorphs, at about 1705 cm$^{-1}$ in infrared spectroscopic analysis; and a polymorph of 2-(3-cyano-4-isobutyloxyphenyl)-4-methyl-5-thiazolecarboxylic acid (crystal G) having characteristic absorptions, which can be distinguished from that of other polymorphs, at about 1703 and 1684 cm$^{-1}$ in infrared spectroscopic analysis.

The present invention also provides an amorphous compound of 2-(3-cyano-4-isobutyloxyphenyl)-4-methyl-5-thiazolecarboxylic acid, which shows an absorption pattern as shown in FIG. 12 in infrared spectroscopic analysis.

Furthermore, the present invention provides a method of producing crystal A, which comprises crystallizing 2-(3-cyano-4-isobutyloxyphenyl)-4-methyl-5-thiazolecarboxylic acid under the conditions shown as the region I in FIG. 1, which are defined by a temperature and a composition of a mixed solvent of methanol and water;

a method of producing crystal D, which comprises recrystallizing 2-(3-cyano-4-isobutyloxyphenyl)-4-methyl-5-thiazolecarboxylic acid under the conditions shown as the region II in FIG. 1, which are defined by a temperature and a composition of a mixed solvent of methanol and water;

a method of producing crystal G, which comprises recrystallizing 2-(3-cyano-4-isobutyloxyphenyl)-4-methyl-5-thiazolecarboxylic acid under the conditions shown as the region III in FIG. 1, which are defined by a temperature and a composition of a mixed solvent of methanol and water;

a method of producing crystal B, which comprises drying crystal G under a reduced pressure with heating;

a method of producing crystal C, which comprises heating 2-(3-cyano-4-isobutyloxyphenyl)-4-methyl-5-thiazolecarboxylic acid suspended in a mixed solvent of methanol and water in the presence of a small amount of crystal C of 2-(3-cyano-4-isobutyloxyphenyl)-4-methyl-5-thiazolecarboxylic acid;

a method of producing crystal G, which comprises recrystallizing of 2-(3-cyano-4-isobutyloxyphenyl)-4-methyl-5-thiazolecarboxylic acid from a mixed solvent of 2-propanol and water;

a method of producing crystal G, which comprises air-drying crystal D under a normal atmosphere; and a method of producing an amorphous compound, which comprises drying crystal D under reduced pressure with heating.

Furthermore, the present invention provides a polymorph (crystal A) obtained by crystallizing 2-(3-cyano-4-isobutyloxyphenyl)-4-methyl-5-thiazolecarboxylic acid under the conditions shown as the region I in FIG. 1, which are defined by a temperature and a composition of a mixed solvent of methanol and water;

a polymorph (crystal D) obtained by crystallizing 2-(3-cyano-4-isobutyloxyphenyl)-4-methyl-5-thiazolecarboxylic acid under the conditions shown as the region II in FIG. 1, which are defined by a temperature and a composition of a mixed solvent of methanol and water;

a polymorph (crystal G) obtained by crystallizing 2-(3-cyano-4-isobutyloxyphenyl)-4-methyl-5-thiazolecarboxylic acid under the conditions shown as the region III in FIG. 1, which are defined by a temperature and a composition of a mixed solvent of methanol and water;

a polymorph (crystal B) of 2-(3-cyano-4-isobutyloxyphenyl)-4-methyl-5-thiazolecarboxylic acid (crystal B) obtained by drying crystal G under reduced pressure with heating;

a polymorph (crystal C) obtained by heating 2-(3-cyano-4-isobutyloxyphenyl)-4-methyl-5-thiazolecarboxylic acid suspended in a mixed solvent of methanol and water in the presence of a small amount of crystal C;

a polymorph (crystal G) obtained by crystallizing 2-(3-cyano-4-isobutyloxyphenyl)-4-methyl-5-thiazolecarboxylic acid from a mixed solvent of 2-propanol and water;

a polymorph (crystal G) of 2-(3-cyano-4-isobutyloxyphenyl)-4-methyl-5-thiazolecarboxylic acid obtained by air-drying crystal D under a normal atmosphere; and an amorphous compound of 2-(3-cyano-4-isobutyloxyphenyl)-4-methyl-5-thiazolecarboxylic acid obtained by drying a polymorph of crystal D under reduced pressure with heating.

BEST MODE FOR CARRYING OUT THE INVENTION

The method of producing various polymorphs according to the present invention includes various methods, and typical examples thereof are as follows.

Figure 1:
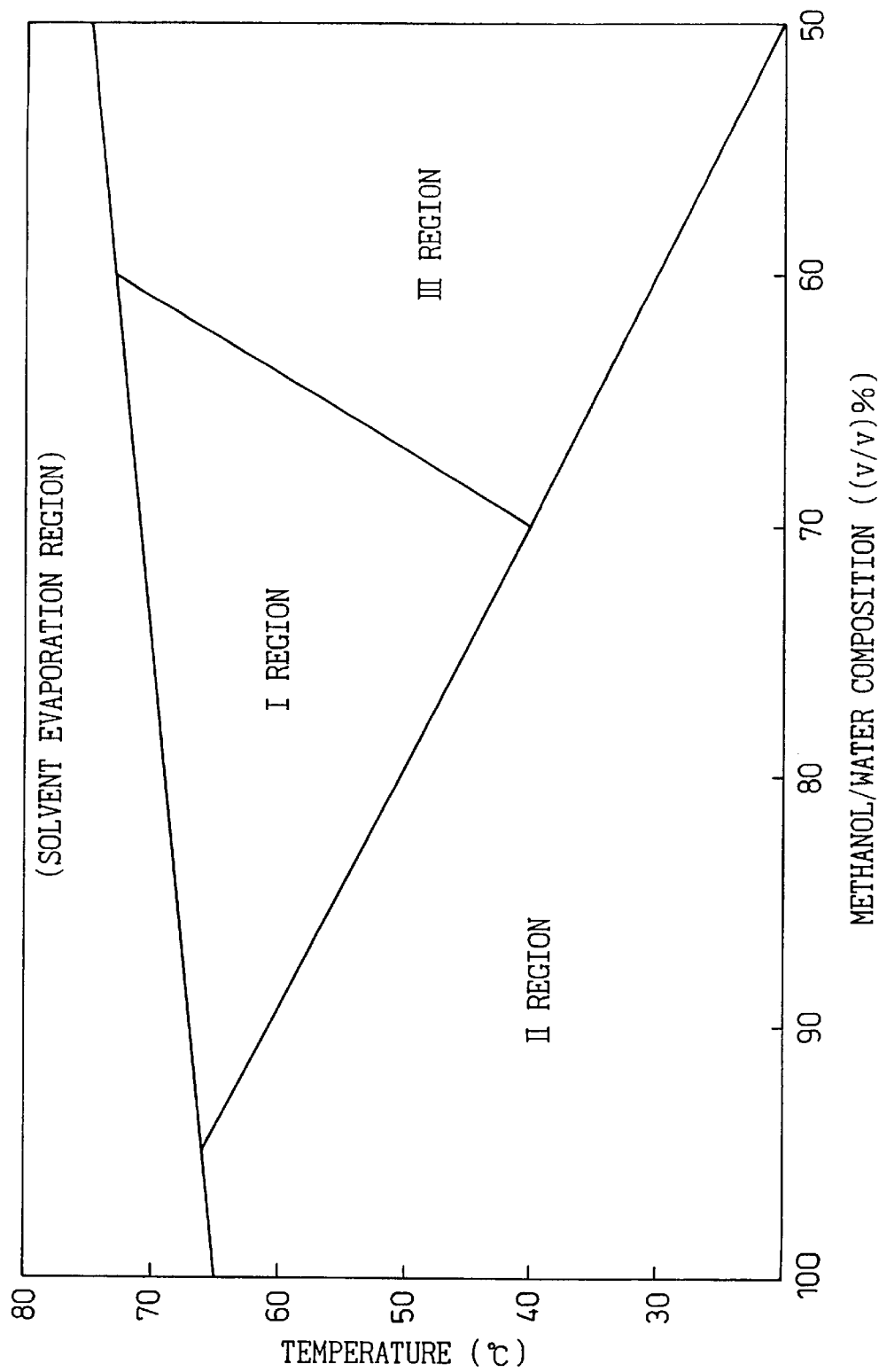
FIG. 1 is a crystallization condition chart for polymorphs of the present invention in methanol/wafer solvent.
Figure 2:
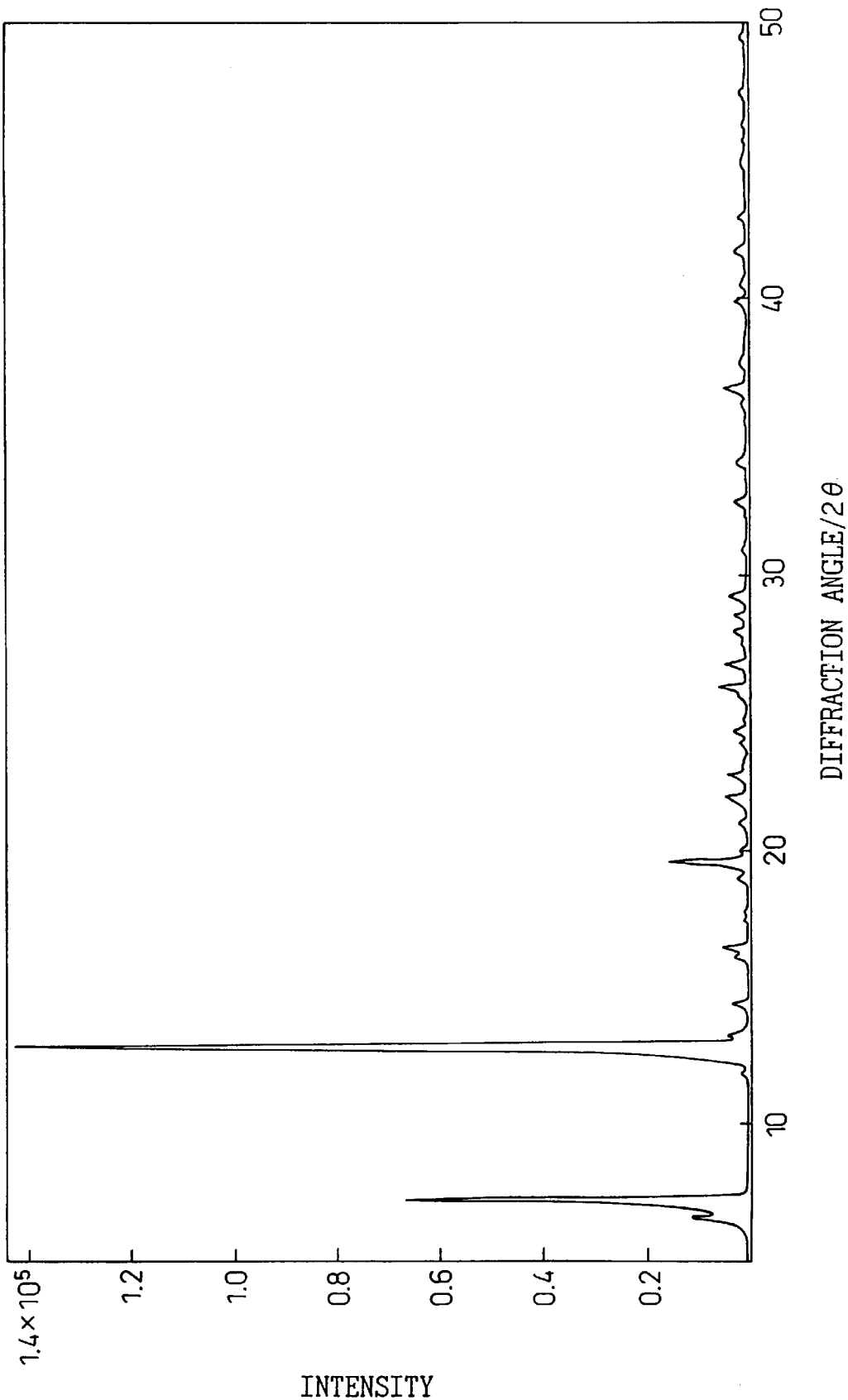
FIG. 2 is a graph showing one embodiment of a XRD pattern of the crystal A of the present invention.
Figure 3:
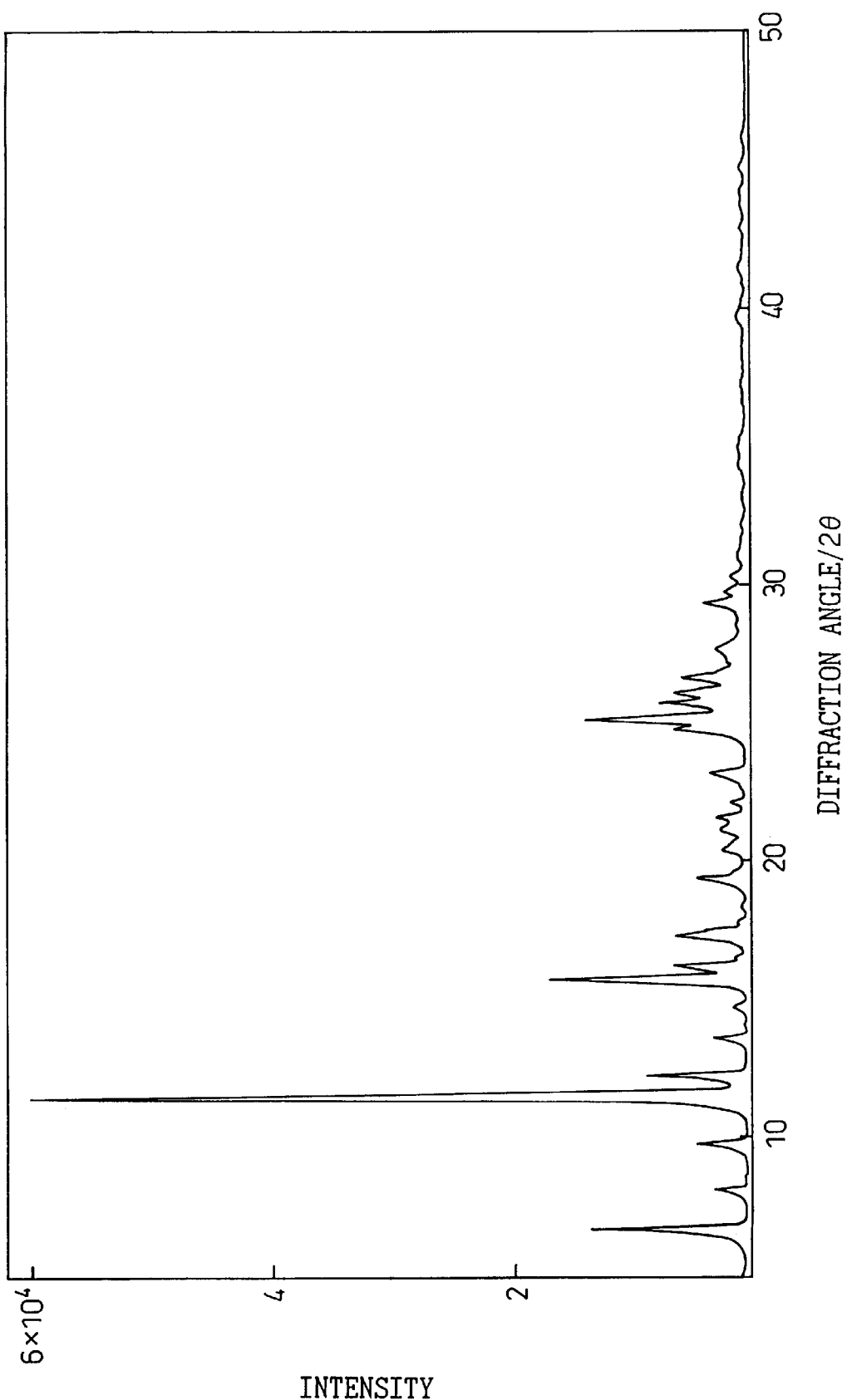
FIG. 3 is a graph showing one embodiment of a XRD pattern of the crystal B of the present invention.
Figure 4:
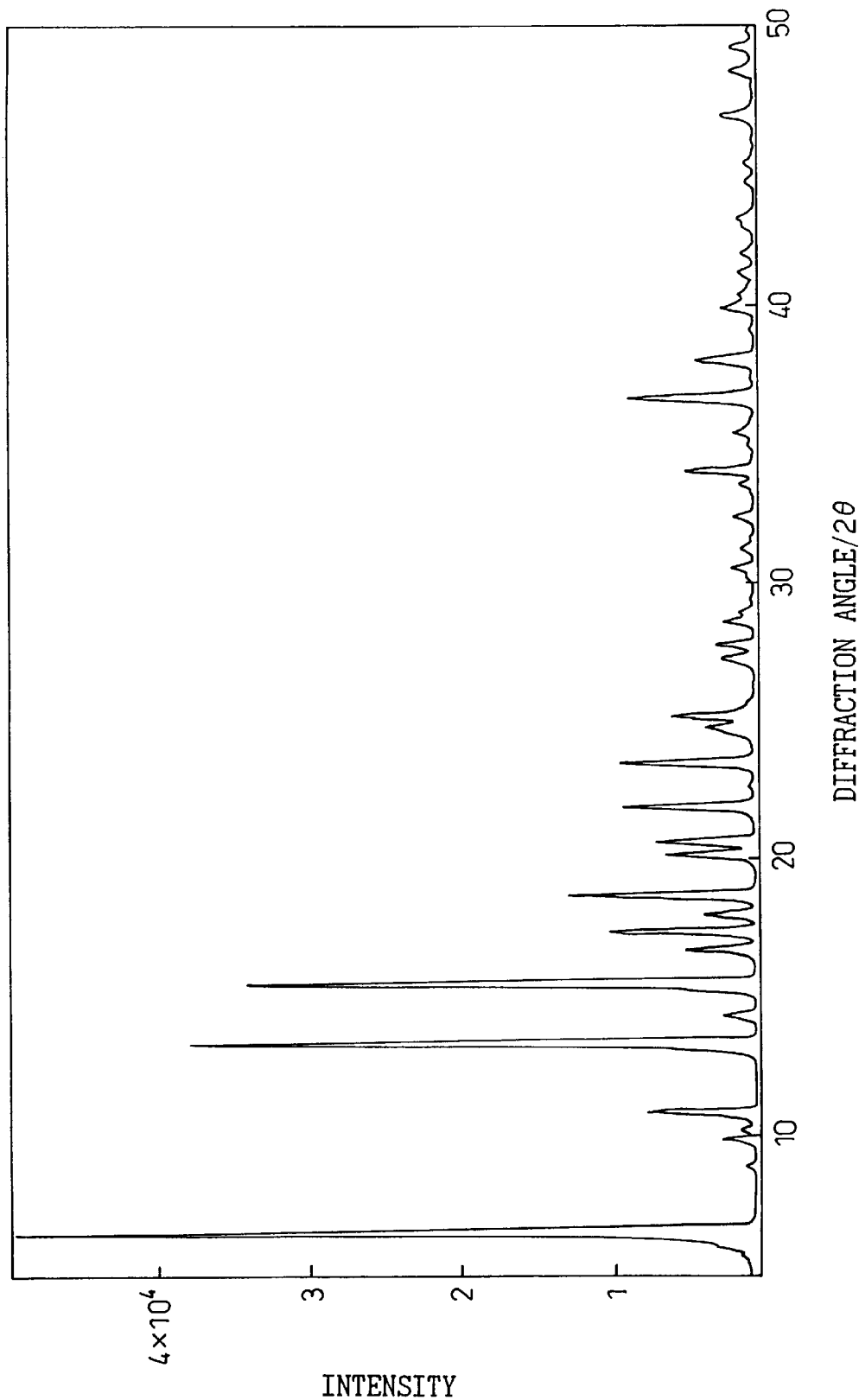
FIG. 4 is a graph showing one embodiment of a XRD pattern of the crystal C of the present invention.
Figure 5:
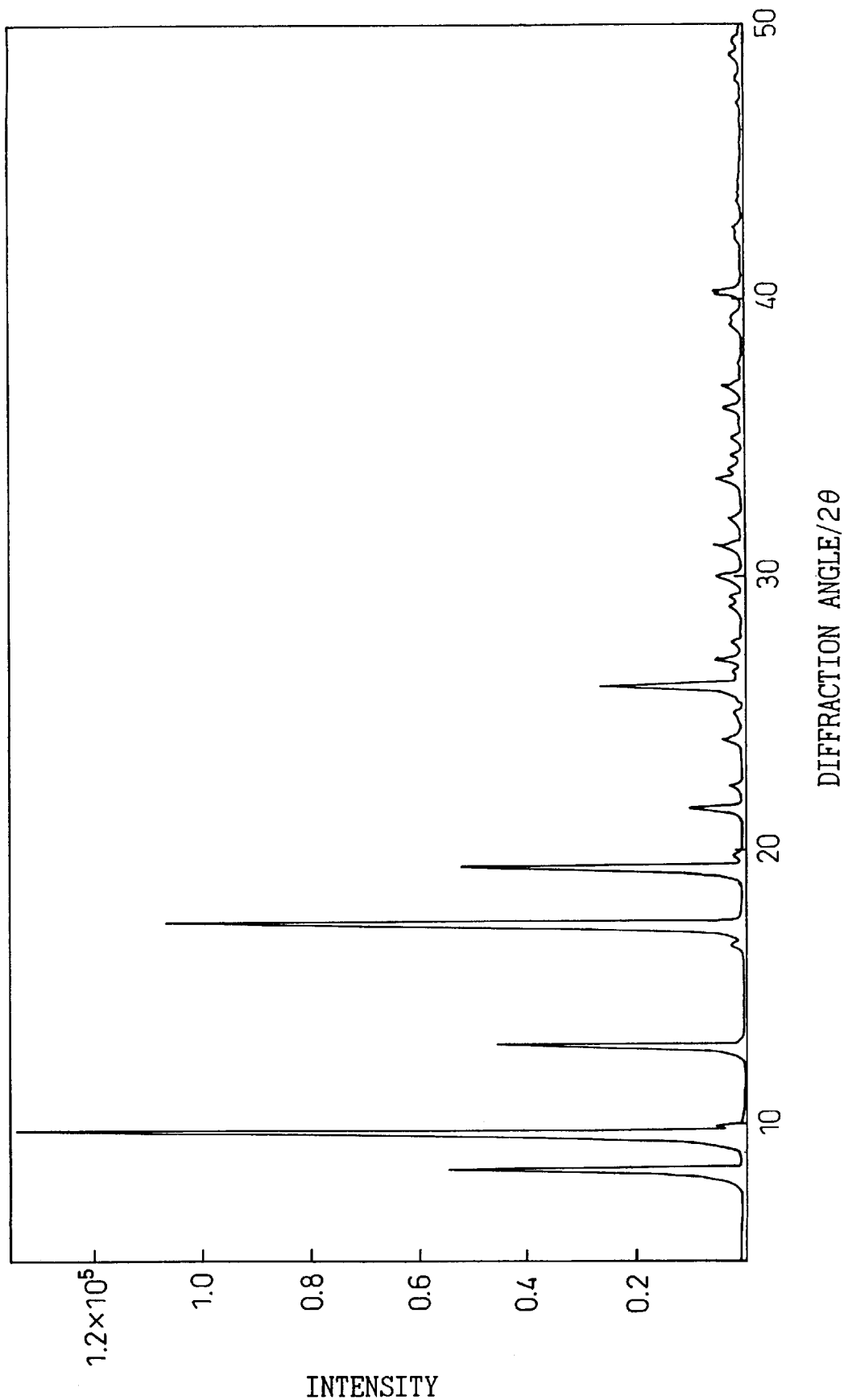
FIG. 5 is a graph showing one embodiment of a XRD pattern of the crystal D of the present invention.
Figure 6:
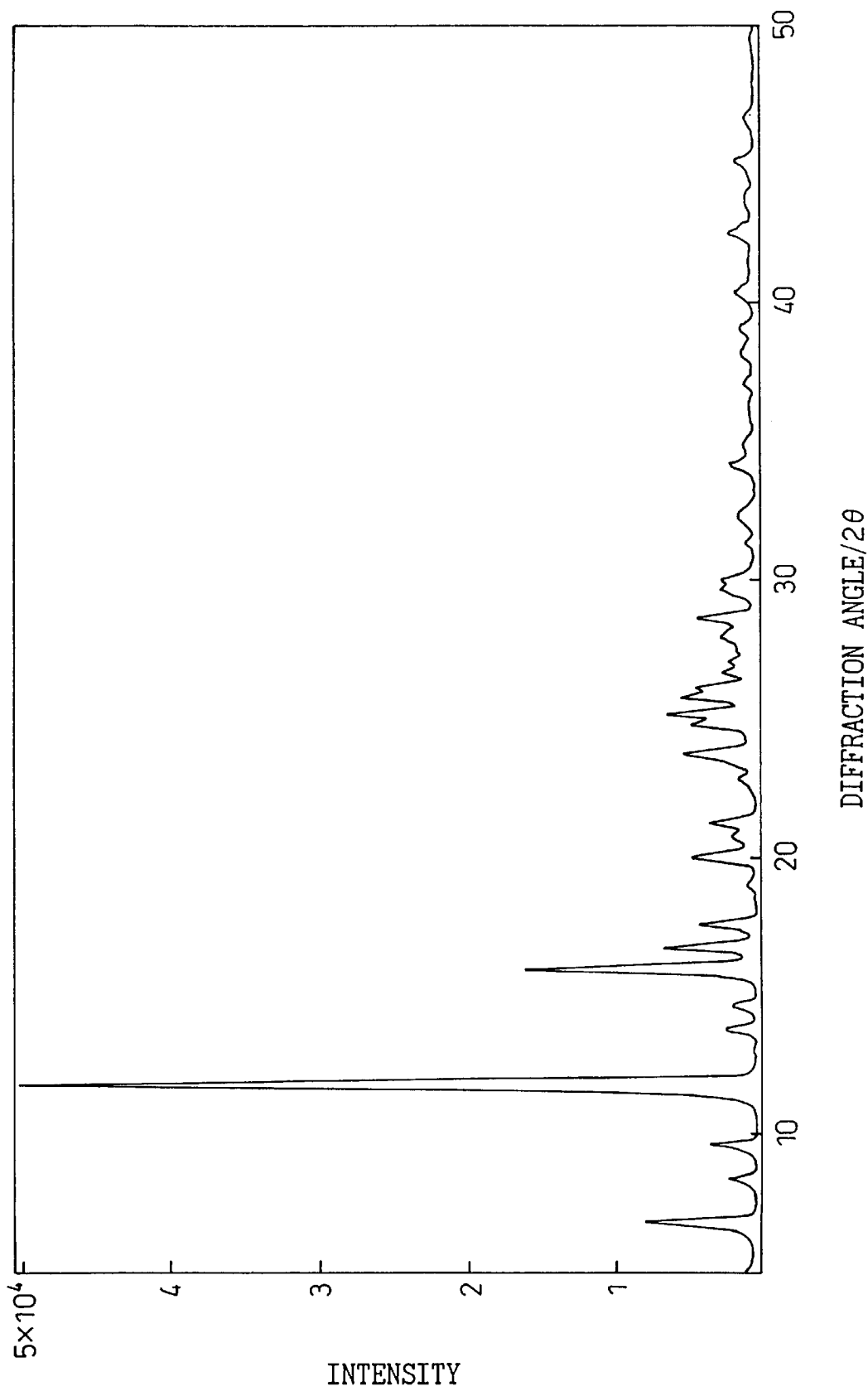
FIG. 6 is a graph showing one embodiment of an XRD pattern of the crystal G of the present invention.
Figure 7:
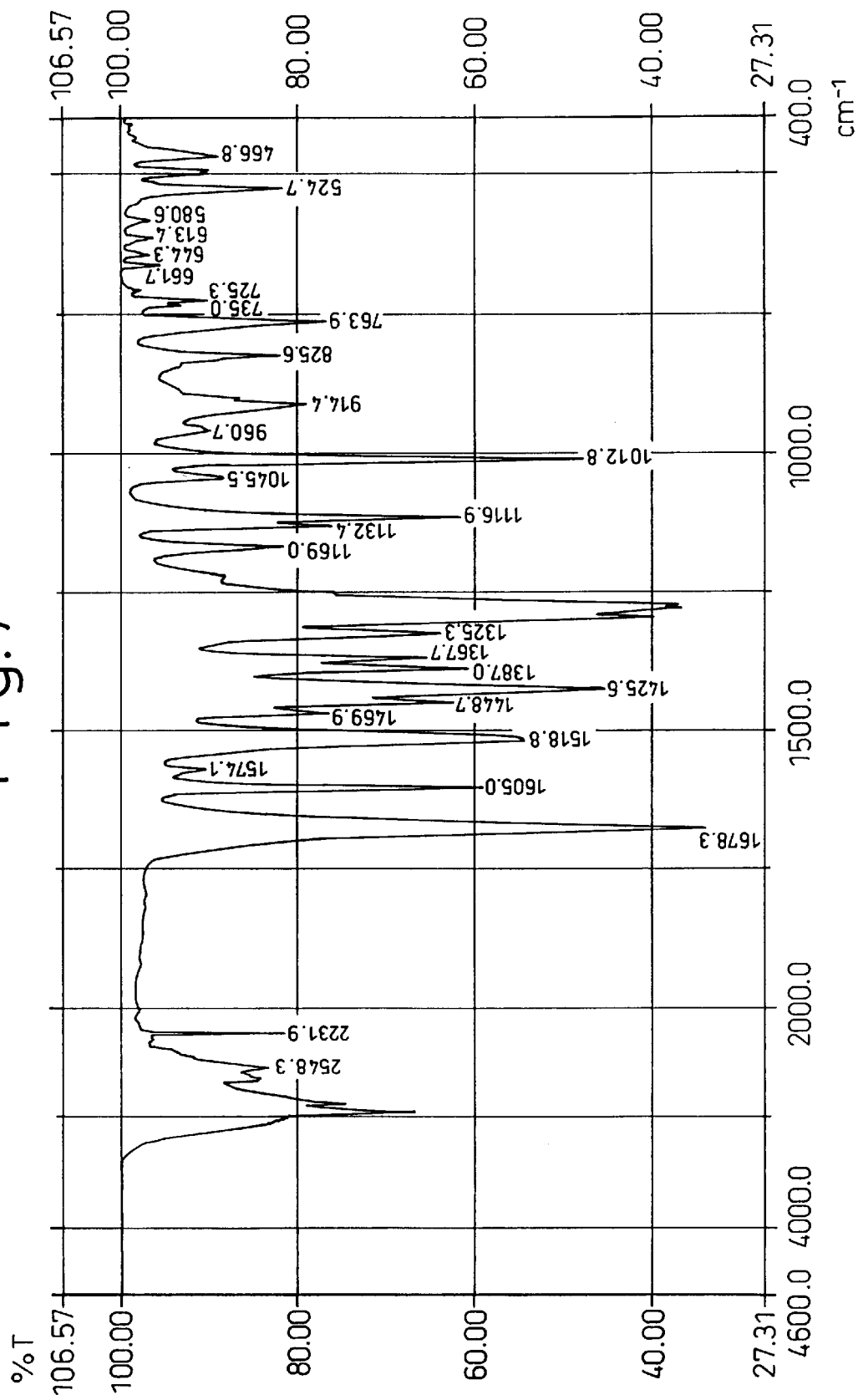
FIG. 7 is a graph showing one embodiment of an IR absorption curve of the crystal A of the present invention.
Figure 8:
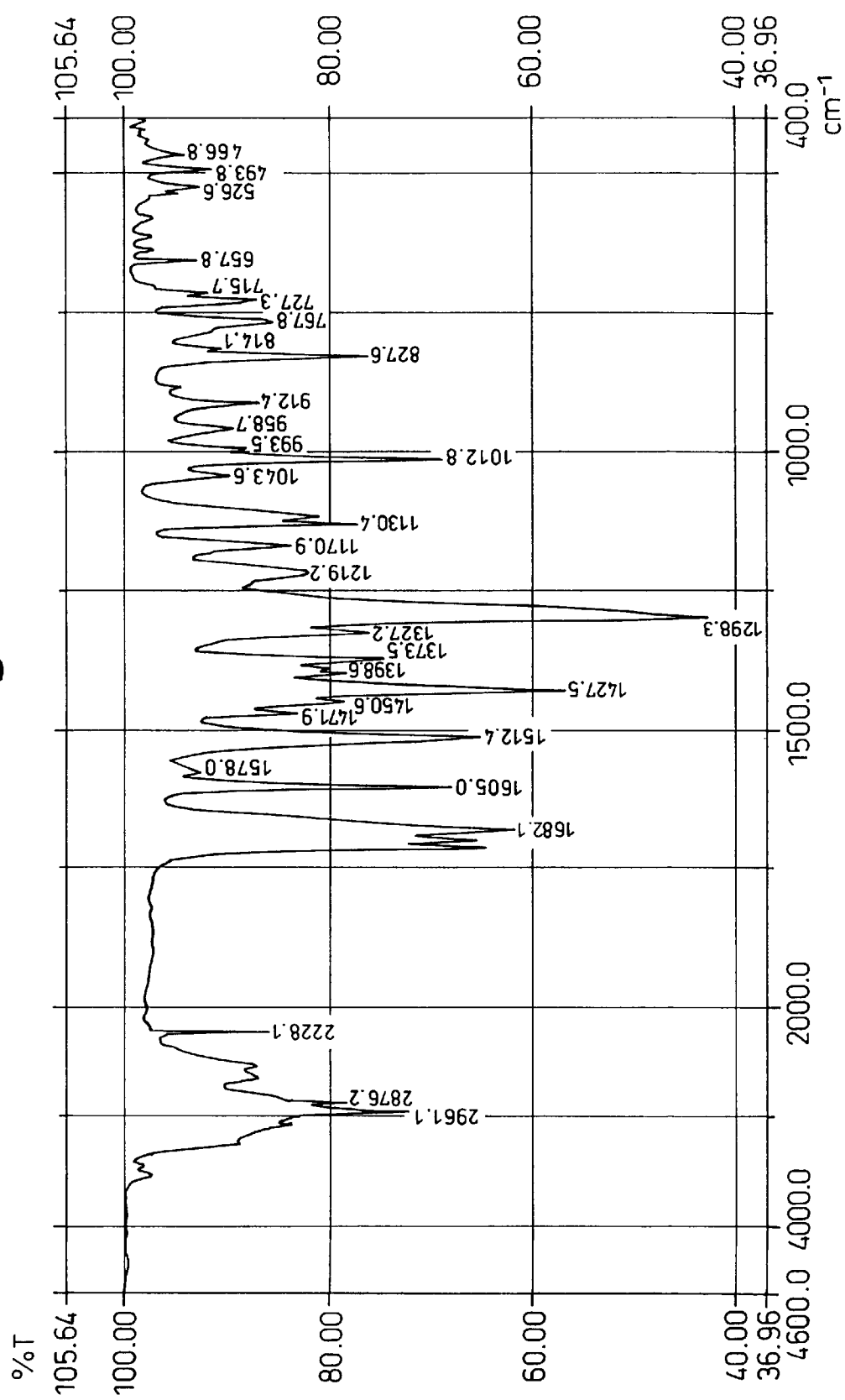
FIG. 8 is a graph showing one embodiment of an IR absorption curve of the crystal B of the present invention.
Figure 9:
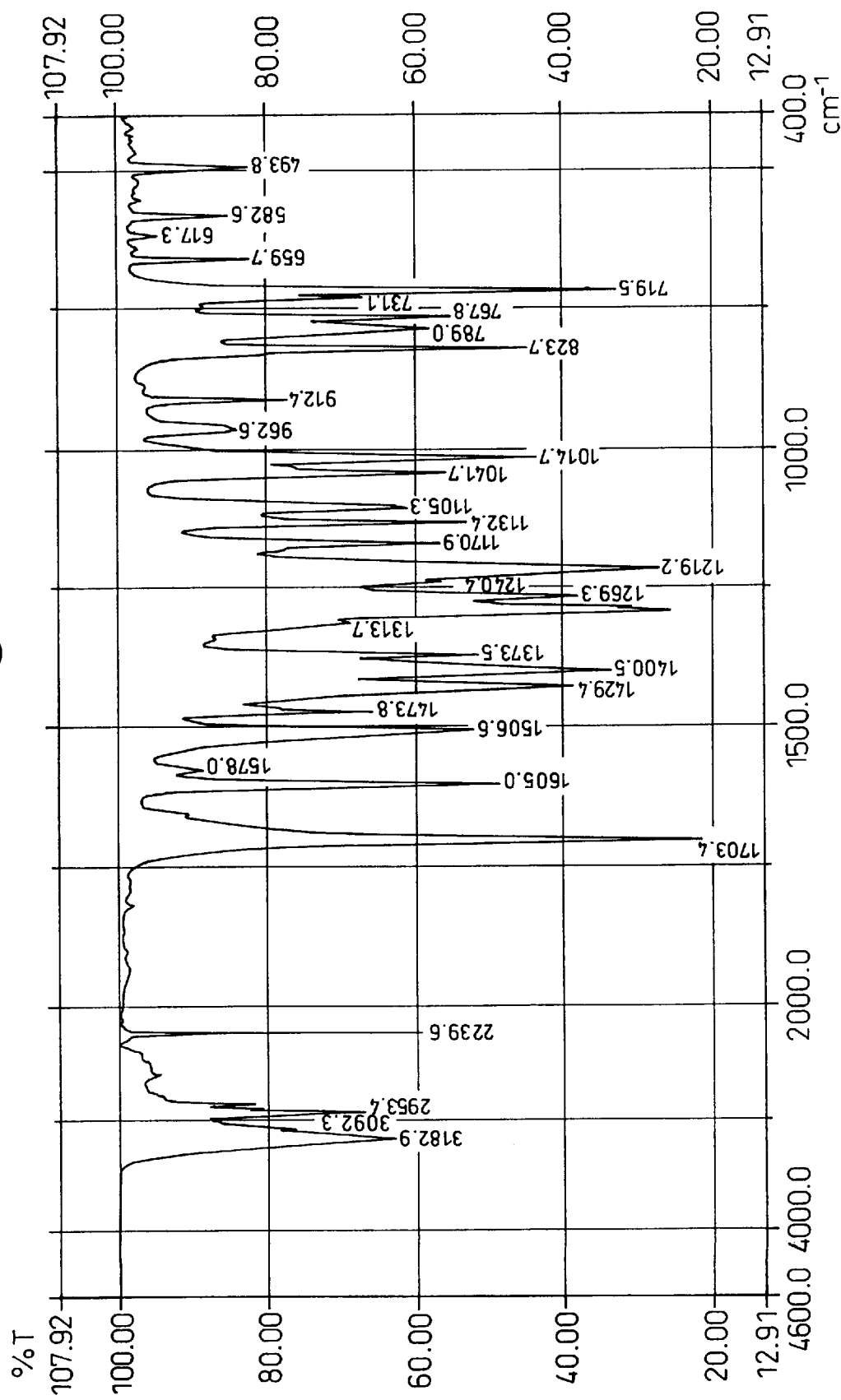
FIG. 9 is a graph showing one embodiment of an IR absorption curve of the crystal C of the present invention.
Figure 10:
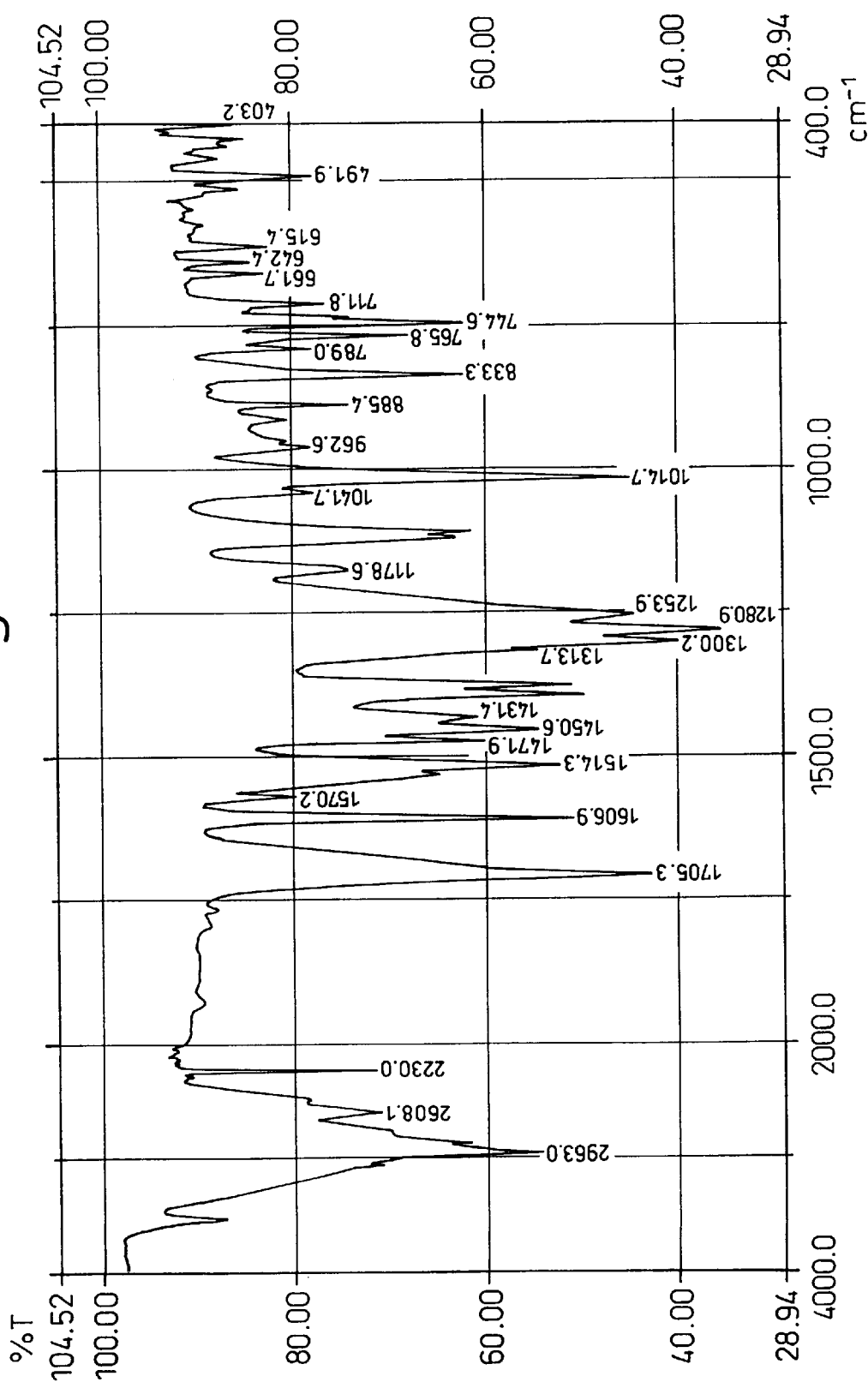
FIG. 10 is a graph showing one embodiment of an IR absorption curve of the crystal D of the present invention.
Figure 11:
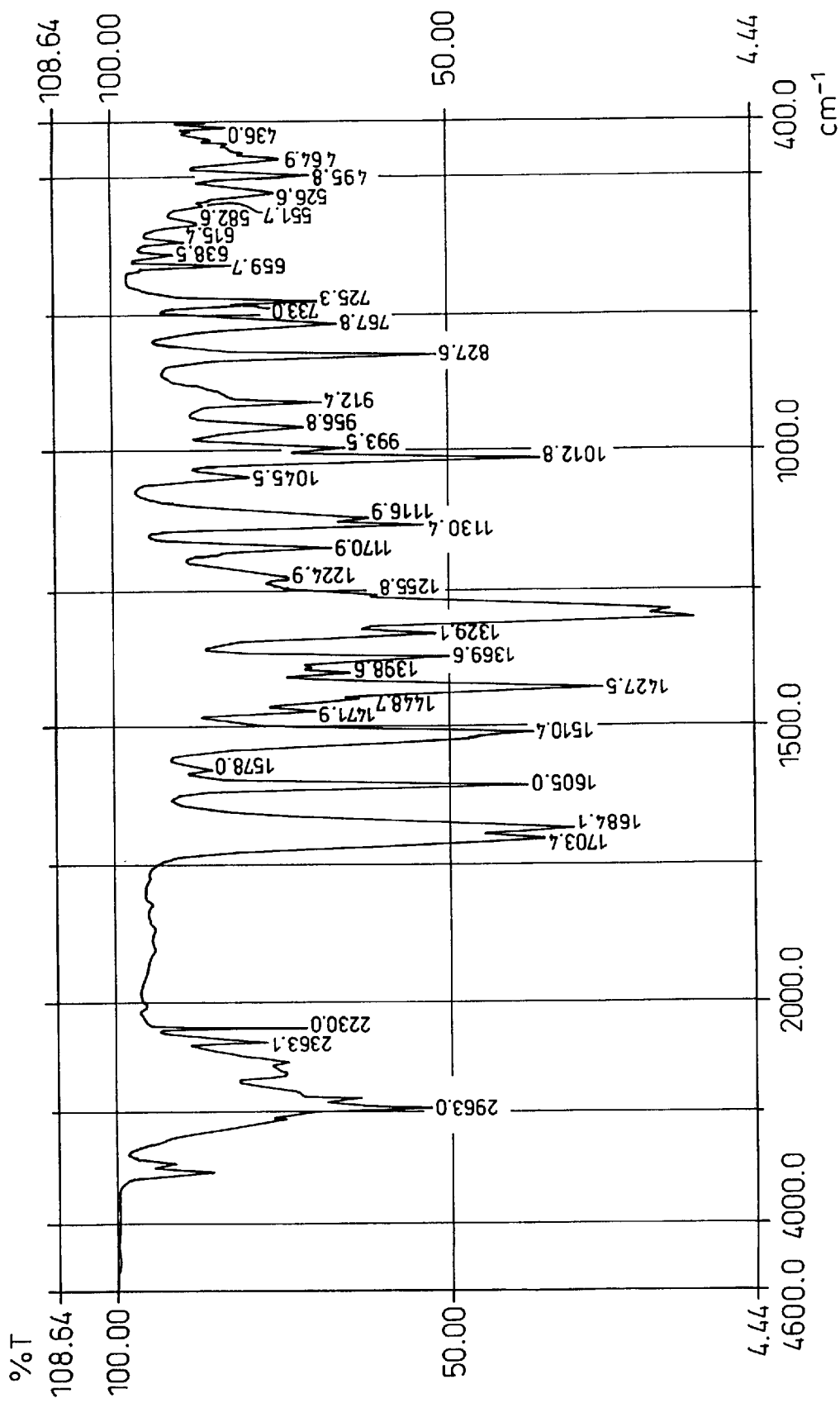
FIG. 11 is a graph showing one embodiment of an IR absorption curve of the crystal G of the present invention.
Figure 12:
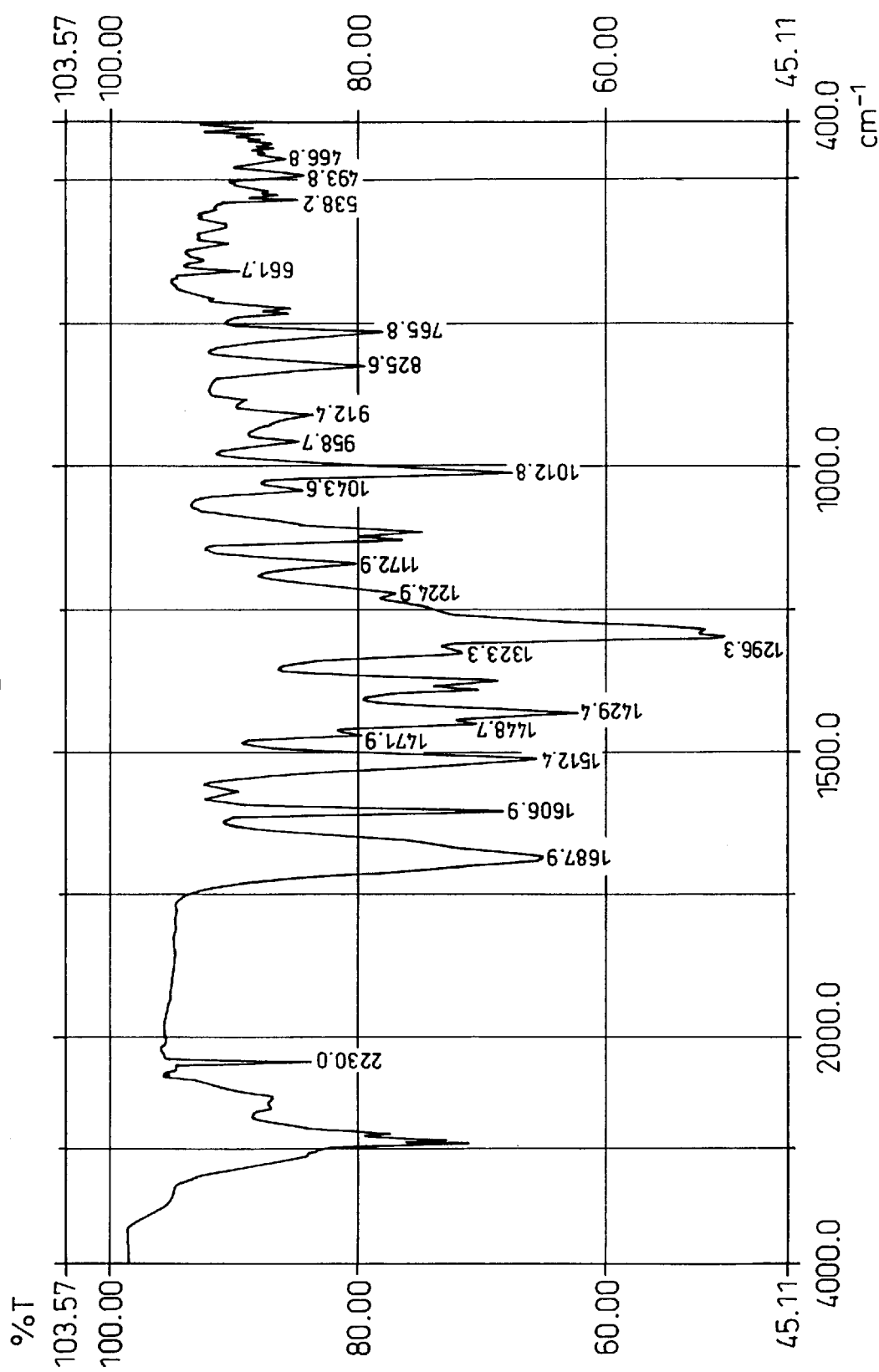
FIG. 12 is a graph showing one embodiment of an IR absorption curve of an amorphous compound of the present invention.

The crystal A is in the form of a metastable crystal form and is obtained under the conditions shown as the region I in FIG. 1, which are defined by a temperature and a composition of a mixed solvent of methanol and water, using a methanol/water reprecipitation method.

The methanol/water reprecipitation method is a method of dissolving 2-(3-cyano-4-isobutyloxyphenyl)-4-methyl-5-thiazolecarboxylic acid in methanol containing water or anhydrous methanol with heating, adding water slowly with stirring, initiating cooling after or during the addition of water, cooling to a predetermined temperature, collecting the crystal by filtration, and drying the crystal.

At this time, the following crystallization condition is preferred to exclusively obtain a desired crystal A. Regarding the solvent used when 2-(3-cyano-4-isobutyloxyphenyl)-4-methyl-5-thiazolecarboxylic acid is dissolved with heating, a ratio of methanol to water is from 100:0 to 80:20, and preferably from 100:0 to 90:10. The dissolving temperature may be 50° C. or higher, but is preferably a reflux temperature. The reason is as follows. That is, if the amount of water is increased or the dissolving temperature is low, the solubility is drastically lowered and a large amount of the solvent must be used so as to dissolve a predetermined amount of 2-(3-cyano-4-isobutyloxyphenyl)-4-methyl-5-thiazolecarboxylic acid with heating, which is not economical. The amount of the solvent is influenced by the composition, but may be an amount capable of completely dissolving it on heating. Specifically, the solvent is added in a 5- to 20-fold, preferably 8- to 15-fold amount by weight relative to the amount of 2-(3-cyano-4-isobutyloxyphenyl)-4-methyl-5-thiazolecarboxylic acid. The reason is as follows. That is, if the amount is too small, chemical purity of the resulting crystal is poor. On the other hand, if the amount of the solvent is too large, it is not economical and the recovery of the purified product is lowered sometimes.

With stirring a uniform solution of 2-(3-cyano-4-isobutyloxyphenyl)-4-methyl-5-thiazolecarboxylic acid, water is added to generate a crystal. In this case, the amount of water to be added can be defined as the amount so that a final ratio of methanol to water is within a range from 70:30 to 55:45. In case where a ratio of methanol to water is about 70:30, a final cooling temperature is preferably adjusted to 45° C. or higher. In case where a ratio of methanol to water is about 60:40, a final cooling temperature is preferably adjusted to 35° C. or higher. In case where a ratio of methanol to water is about 55:45, a final cooling temperature is preferably adjusted to 30° C. or higher. Cooling is preferably initiated after the ratio of methanol to water reaches about 80:20, but may be initiated immediately after the completion of the addition of water.

Any crystal form of 2-(3-cyano-4-isobutyloxyphenyl)-4-methyl-5-thiazolecarboxylic acid can be used as far as the crystal is dissolved completely before the addition of water is initiated.

The temperature of water to be added is not critical, but may be controlled in case where an internal temperature change is expected depending on a scale of an operation. The temperature is suitably within a range from 5 to 95° C., but is preferably from about room temperature to 80° C. A small amount of the crystal A as a seed crystal of the crystal A may be suspended in water to be added.

A crystal B is obtained by drying a crystal G under reduced pressure with heating. In this case, the heating temperature is usually 50° C. or higher, and preferably from 65 to 100° C. If the temperature is too low, it takes a long time to release water of crystallization, which is not suited for practical use. On the other hand, if the temperature is too high, the chemical purity is likely to be lowered by decomposition of the desired substance. The vacuum degree is adjusted according to the heating temperature, but is usually 25 mmHg or less, preferably several mmHg or less.

Crystal C is produced by solvent-mediated polymorphic transition. The solvent to be used is preferably a solvent in which 2-(3-cyano-4-isobutyloxyphenyl)-4-methyl-5-thiazolecarboxylic acid is slightly soluble. A mixed solution of methanol and water is usually used. The ratio of methanol to water is from 80:20 to 50:50, and preferably from 70:30 to 60:40. An excess crystal is suspended in such a solvent and a small amount of crystal C is added, followed by heating with stirring. The amount of the crystal C to be added or heating temperature exerts an influence on the completion time of the conversion into the crystal C. Generally, the amount of the crystal C is preferably 2% by weight or less relative to the amount of 2-(3-cyano-4-isobutyloxyphenyl)-4-methyl-5-thiazolecarboxylic acid to be converted into the crystal C, and usually 1% by weight or less. The crystal form of 2-(3-cyano-4-isobutyloxyphenyl)-4-methyl-5-thiazolecarboxylic acid to be converted into the crystal C does not exert an influence on the results of the conversion. The heating temperature exerts an influence on the time required to complete the conversion, but it is not critical as far as the conversion occurs finally. The heating temperature is generally 50° C. or higher, and usually 60° C. or higher.

Crystal D is a methanolate and is obtained by drying a wet product, which has been obtained by recrystallizing from a methanol solvent or a mixed solvent of methanol and water, at a low temperature under a reduced pressure. When this wet product is air-dried at a room temperature under a normal pressure, crystal G is obtained. On the other hand, when the wet product is dried at a high temperature under a reduced pressure, an amorphous compound is obtained. Regarding the drying condition for obtaining the crystal D, the temperature is usually 35° C. or lower, and preferably 25° C. or lower. In case where the wet product is dried at a room temperature under a reduced pressure to obtain an amorphous compound, the heating temperature is usually 50° C. or higher, and preferably from 65 to 100° C. If the heating temperature is too low, it takes a long time to release methanol, which is not suited for practical use. On the other hand, if the temperature is too high, the chemical purity is likely to be lowered by decomposition of the desired substance. The vacuum degree is adjusted according to the heating temperature, but is usually 25 mmHg or less, preferably several mmHg or less. Another method for obtaining the above-described wet product includes a methanol/water reprecipitation method for obtaining the crystal A, wherein the addition of water is terminated when the ratio of methanol to water reached 70:30 and the mixture is cooled as it is and stirred for a long time. In this case, the temperature on stirring for a long time varies depending on the amount of methanol, but the desired wet product can be obtained by maintaining the temperature at 30° C. or lower in case where the ratio of methanol to water is 70:30.

The crystal G is a hydrate and is obtained by crystallizing a sodium salt of 2-(3-cyano-4-isobutyloxyphenyl)-4-methyl-5-thiazolecarboxylic acid from an acid, or drying a wet product, which has been obtained by recrystallization from a mixed solvent of 2-propanol and water, at low temperature under a reduced pressure or air-drying the wet product under a normal pressure. It was previously described that crystal B is obtained when the resulting wet product is dried under a reduced pressure with heating. The ratio of 2-propanol to water is from about 90:10 to 50:50. However, when the amount of water increases, the solubility is drastically lowered and, therefore, it is necessary to properly select the amount. The amount of the mixed solvent of 2-propanol and water is not a critical factor, but the mixed solvent is used in a 5- to 20-fold, preferably 8- to 15-fold amount by weight relative to the amount of 2-(3-cyano-4-isobutyloxyphenyl)-4-methyl-5-thiazolecarboxylic acid to be used usually. The crystal G is also obtained by air-drying a wet product of the crystal D, which is obtained by the above-described method, at room temperature under a normal pressure.

On the other hand, an amorphous compound can be obtained by drying the crystal D under a reduced pressure with heating. In this case, the heating temperature is usually 50° C. or higher, and preferably from 65 to 100° C. If the heating temperature is too low, it takes a long time to release methanol contained, which is not suited for practical use. On the other hand, too high temperature should be avoided to prevent lowering of the chemical purity caused by decomposition of the desired substance. The vacuum degree is adjusted according to the heating temperature, but is usually 25 mmHg or less, preferably several mmHg or less.

Each of these various polymorphs of the present invention has characteristics for industrial production and physico-chemical characteristics for original drugs as described below.

The crystal A is positioned as a metastable crystal within a normal operation range in the region I. This crystal form is retained for a long period of time under normal storage conditions (e.g. relative humidity of 75%, 25° C., etc.) and is chemically stable.

The crystal C is positioned as a stable crystal within a normal operation range in the region I. However, solvent-mediated polymorphic transition into this crystal form usually requires several days and it is difficult to produce the crystal C in an industrially good reproducible manner. Therefore, it was necessary that the conversion is attained in a short time by accelerating the conversion by a certain method. To accelerate the conversion, an operation of adding a seed crystal of the crystal C in a state where the crystal is suspended, and heating again is required. This crystal form is retained for a long period of time under normal storage conditions (e.g. relative humidity of 75%, 25° C., etc.) and is chemically stable.

The crystal G loses water of crystallization by an operation of drying under a reduced pressure with heating, thereby changing into crystal B. This crystal form is retained for a long period of time under normal storage conditions (e.g. relative humidity of 75%, 25° C., etc.) and is chemically stable.

The crystal B absorbs water, thereby to be converted into crystal G in case where the crystal B is stored under normal storage condition (e.g. relative humidity of 75%, 25° C., etc.). That is, the crystal G can be produced only by allowing to stand the crystal B under a normal humidity condition and is a significant crystal form in a respect that various crystal forms can be selectively made.

In the same manner as in case of the crystal B, the crystal D is converted into crystal G only by allowing to stand under a normal humidity condition and is a significant crystal form in a respect that various crystal forms can be selectively made. The crystal D is only one intermediate capable of producing an amorphous compound by drying it under reduced pressure with heating.

As described above, any crystal form is useful, but crystals A, C and G are useful in view of retention of crystal form due to storage for a long period of time. Among them, a crystal A is preferred in view of industrial superiority.

EXAMPLES

The following examples further illustrate the present invention in detail, but the present invention is not limited by these examples.

Example 1

Production of crystal A of 2-(3-cyano-4-isobutyloxyphenyl)-4-methyl-5-thiazolecarboxylic acid To 10 g of 2-(3-cyano-4-isobutyloxyphenyl)-4-methyl-5-thiazolecarboxylic acid, 114 mL of methanol was added and the compound was dissolved by heating to 65° C. with stirring. To the resulting solution, 114 ml of water in which 20 mg of crystal A of 2-(3-cyano-4-isobutyloxyphenyl)-4-methyl-5-thiazolecarboxylic acid was added over 1 hour. Then, the mixed solution was cooled to 35° C. The crystal was collected by filtration and dried at 80° C. under a reduced pressure of 2 mmHg for 4 hours. As is apparent from data of XRD and IR, the resulting crystal was crystal A.

Example 2

Production of crystal C of 2-(3-cyano-4-isobutyloxyhenyl-4-methyl-5-thiazolecarboxylic acid To 10 g of 2-(3-cyano-4-isobutyloxyphenyl)-4-methyl-5-thiazolecarboxylic acid, 100 mL of a mixed solution of methanol and water in a mixing ratio of 70:30 was added, followed by heating to 65° C. with stirring. To the resulting solution, 20 mg of crystal C of 2-(3-cyano-4-isobutyloxyphenyl)-4-methyl-5-thiazolecarboxylic acid was added. The crystal was collected and stirred until conversion into a crystal C is confirmed by IR. After cooling, the crystal was collected by filtration and dried at 80° C. under a reduced pressure of 2 mmHg for 4 hours. As is apparent from data of XRD and IR, the resulting crystal was crystal C.

Example 3

Production of crystal D of 2-(3-cyano-4-isobutyloxyphenyl)-4-methyl-5-thiazolecarboxylic acid To 10 g of 2-(3-cyano-4-isobutyloxyphenyl)-4-methyl-5-thiazolecarboxylic acid, 80 mL of methanol was added, followed by heating to 65° C. with stirring. Then, the crystal was collected and stirred until conversion into crystal C was confirmed by IR. After cooling, the crystal was collected by filtration and dried at 25° C. under a reduced pressure of 2 mmHg for 4 hours. As is apparent from data of XRD and IR, the resulting crystal was crystal D.

Example 4

Production of crystal G of 2-(3-cyano-4-isobutyloxyphenyl)-4-methyl-5-thiazolecarboxylic acid To 10 g of 2-(3-cyano-4-isobutyloxyphenyl)-4-methyl-5-thiazolecarboxylic acid, 90 mL of methanol was added and the compound was dissolved by heating to 65° C. with stirring. To the mixture, 90 mL of water was added over 30 seconds. The solution was cooled to 25° C. The crystal was collected by filtration and air-dried for 2 days. As is apparent from data of XRD and IR, the resulting crystal was crystal G.

Example 5

Production of crystal G of 2-(3-cyano-4-isobutyloxyphenyl-4-methyl-5-thiazolecarboxylic acid (recrystallization from 2-propanol/water solvent)

To 30 g of 2-(3-cyano-4-isobutyloxyphenyl)-4-methyl-5-thiazolecarboxylic acid, 900 mL of a mixed solution of 2-propanol and water in a mixing ratio of 50:50 was added, followed by heating to 80° C. with stirring. This mixture was filtered in a hot state, dissolved again with heating and then cooled to a room temperature. The deposited crystal was collected by filtration and air-dried on a filter paper overnight. As a result of Karl Fisher's water content measurement, the resulting crystal had a water content of 2.7% by weight. As is apparent from data of XRD and IR, the resulting crystal was crystal G.

Example 6

Production of crystal G of 2-(3-cyano-4-isobutyloxyphenyl)-4-methyl-5-thiazolecarboxylic acid (recrystallization from methanol/water solvent)

33.4 g of 2-(3-cyano-4-isobutyloxyphenyl)-4-methyl-5-thiazolecarboxylic acid was dissolved in 334 mL of a mixture of methanol and water in a mixing ratio of 95:5 by heating with stirring. While the mixture was heated with reflux at an external temperature of 85° C., 119 mL of water was added gradually. Then, 150 mg of crystal C was added and the mixture was continuously heated at reflux for 4 hours. After cooling, the reaction product was dried at 80° C. under a reduced pressure of 2 mmHg with heating for 6 hours to obtain 33 g of crystal G. As is apparent from data of XRD and IR, the resulting crystal was crystal G.

Example 7

Production of crystal G of 2-(3-cyano-4-isobutyloxyphenyl)-4-methyl-5-thiazolecarboxylic acid production from crystal D)

The resulting crystal D obtained in Example 3 was air-dried on a filter paper overnight. As a result of Karl Fisher's water content measurement, the resulting crystal had a water content of 2.6% by weight. As is apparent from data of XRD and IR, the resulting crystal was crystal G.

Example 8

Production of crystal B of 2-(3-cyano-4-isobutyloxyphenyl)-4-methyl-5-thiazolecarboxylic acid The crystal G obtained in Example 4 was dried at 80° C. under a reduced pressure of 2 mmHG with heating for 2 days. As is apparent from data of XRD and IR, the resulting crystal was crystal B.

Example 9

Production of amorphous compound of 2-(3-cyano-4-isobutyloxyphenyl)-4-methyl-5-thiazolecarboxylic acid The crystal D obtained in Example 3 was dried at 80° C. under a reduced pressure of 2 mmHg with heating for 4 days. As is apparent from data of XRD and IR, the resulting crystal was amorphous compound.

Example 10

Stability Test

The stability test of the crystals A, B, C, D and G was conducted under the following conditions.

Storage condition 1: stored under conditions of 40° C./75% relative density in a sealed state for 3 and 6 months.

Storage condition 2: stored under conditions of 40° C./75% relative density in an unsealed state for 1 and 3 months.

As a result, conversion of crystals B and D into crystal G could be confirmed by X-ray powder diffraction and infrared spectroscopic analysis after three months under the storage condition 1 and after one month under the storage condition 2. It was confirmed that the crystal G after conversion retains a crystal form of the crystal G after six months under the storage condition 1 and after three months under the storage condition 2.

On the other hand, conversion of the crystals A, C and G into other polymorphs could not be confirmed after six months under the storage condition 1 and after three months under the storage condition 2.

During the whole test period, no change in total amount of impurities of each polymorph was recognized as compared with that before the beginning of the test.

What is claimed is:

1. A polymorph of 2-(3-cyano-4-isobutyloxyphenyl)-4-methyl-5-thiazolecarboxylic acid, which shows a X-ray powder diffraction pattern having characteristic peaks at a reflection angle 2θ of about 6.62, 7.18, 12.80, 13.26, 16.48, 19.58, 21.92, 22.68, 25.84, 26.70, 29.16 and 36.70°.

2. A polymorph of 2-(3-cyano-4-isobutyloxyphenyl)-4-methyl-5-thiazolecarboxylic acid, which shows a X-ray powder diffraction pattern having characteristic peaks at a reflection angle 2θ of about 6.76, 8.08, 9.74, 11.50, 12.22, 13.56, 15.76, 16.20, 17.32, 19.38, 21.14, 21.56, 23.16, 24.78, 25.14, 25.72, 26.12, 26.68, 27.68 and 29.36°.

3. A polymorph of 2-(3-cyano-4-isobutyloxyphenyl)-4-methyl-5-thiazolecarboxylic acid, which shows a X-ray powder diffraction pattern having characteristic peaks at a reflection angle 2θ of about 6.62, 10.82, 13.36, 15.52, 16.74, 17.40, 18.00, 18.70, 20.16, 20.62, 21.90, 23.50, 24.78, 25.18, 34.08, 36.72 and 38.04°.

4. A polymorph of 2-(3-cyano-4-isobutyloxyphenyl)-4-methyl-5-thiazolecarboxylic acid, which shows a X-ray powder diffraction pattern having characteristic peaks at a reflection angle 2θ of about 8.32, 9.68, 12.92, 16.06, 17.34, 19.38, 21.56, 24.06, 26.00, 30.06, 33.60 and 40.34°.

5. A polymorph of 2-(3-cyano-4-isobutyloxyphenyl)-4-methyl-5-thiazolecarboxylic acid, which shows a X-ray powder diffraction pattern having characteristic peaks at a reflection angle 2θ of about 6.86, 8.36, 9.60, 11.76, 13.74, 14.60, 15.94, 16.74, 17.56, 20.00, 21.26, 23.72, 24.78, 25.14, 25.74, 26.06, 26.64, 27.92, 28.60, 29.66 and 29.98°.

6. A polymorph of 2-(3-cyano-4-isobutyloxyphenyl)-4-methyl-5-thiazolecarboxylic acid having a characteristic absorption, which can be distinguished from that of other polymorphs, at about 1678 $cm^{-1}$ in infrared spectroscopic analysis.

7. A polymorph of 2-(3-cyano-4-isobutyloxyphenyl)-4-methyl-5-thiazolecarboxylic acid having characteristic absorptions, which can be distinguished from that of other polymorph, at about 1715, 1701 and 1682 $cm^{-1}$ in infrared spectroscopic analysis.

8. A polymorph of 2-(3-cyano-4-isobutyloxyphenyl)-4-methyl-5-thiazolecarboxylic acid having characteristic absorptions, which can be distinguished from that of other polymorph, at about 1703 and 1219 $cm^{-1}$ in infrared spectroscopic analysis.

9. A polymorph of 2-(3-cyano-4-isobutyloxyphenyl)-4-methyl-5-thiazolecarboxylic acid having a characteristic absorption, which can be distinguished from that of other polymorph, at about 1705 $cm^{-}$ in infrared spectroscopic analysis.

10. A polymorph of 2-(3-cyano-4-isobutyloxyphenyl)-4-methyl-5-thiazolecarboxylic acid having characteristic absorptions, which can be distinguished from that of other polymorph, at about 1703 and 1684 $cm^{-1}$ in infrared spectroscopic analysis.

11. An amorphous compound of 2-(3-cyano-4-isobutyloxyphenyl)-4-methyl-5-thiazolecarboxylic acid.

12. A polymorph obtained by crystallizing 2-(3-cyano-4-isobutyloxyphenyl)-4-methyl-5-thiazolecarboxylic acid under the conditions shown as the region I in FIG. 1, which are defined by a temperature and a composition of a mixed solvent of methanol and water.

13. A polymorph obtained by crystallizing 2-(3-cyano-4-isobutyloxyphenyl)-4-methyl-5-thiazolecarboxylic acid under the conditions shown as the region II in FIG. 1, which are defined by a temperature and a composition of a mixed solvent of methanol and water.

14. A polymorph obtained by crystallizing 2-(3-cyano-4-isobutyloxyphenyl)-4-methyl-5-thiazolecarboxylic acid under the conditions shown as the region III in FIG. 1, which are defined by a temperature and a composition of a mixed solvent of methanol and water.

15. A polymorph obtained by drying crystal G of 2-(3-cyano-4-isobutyloxyphenyl)-4-methyl-5-thiazolecarboxylic acid under a reduced pressure with heating.

16. A polymorph obtained by heating 2-(3-cyano-4-isobutyloxyphenyl)-4-methyl-5-thiazolecarboxylic acid suspended in a mixed solvent of methanol and water in the presence of a small amount of a crystal C of 2-(3-cyano-4-isobutyloxyphenyl)-4-methyl-5-thiazolecarboxylic acid.

17. A polymorph obtained by crystallizing 2-(3-cyano-4-isobutyloxyphenyl)-4-methyl-5-thiazolecarboxylic acid from a mixed solvent of 2-propanol and water.

18. A polymorph obtained by air-drying crystal D of 2-(3-cyano-4-isobutyloxyphenyl)-4-methyl-5-thiazolecarboxylic acid under a normal atmosphere.

19. An amorphous compound obtained by drying crystal D of 2-(3-cyano-4-isobutyloxyphenyl)-4-methyl-5-thiazolecarboxylic acid under a reduced pressure with heating.

20. A method of producing crystal A of 2-(3-cyano-4-isobutyloxyphenyl)-4-methyl-5-thiazolecarboxylic acid, which comprises crystallizing under the conditions shown as region I in FIG. 1, which are defined by a temperature and a composition of a mixed solvent of methanol and water,
wherein region I is an area surrounded by lines defined by $Y=-0.2X+85$; $Y=1.0X-31$; and $Y=-3.3X+273$,
wherein X is methanol/water composition (U/V %), and Y is temperature (° C.).

21. A method of producing crystal B of 2-(3-cyano-4-isobutyloxyphenyl)-4-methyl-5-thiazolecarboxylic acid, which comprises drying crystal G of 2-(3-cyano-4-isobutyloxyphenyl)-4-methyl-5-thiazolecarboxylic acid under a reduced pressure with heating.

22. A method of producing crystal C of 2-(3-cyano-4-isobutyloxyphenyl)-4-methyl-5-thiazolecarboxylic acid, which comprises heating 2-(3-cyano-4-isobutyloxyphenyl)-4-methyl-5-thiazolecarboxylic acid suspended in a mixed solvent of methanol and water in the presence of a small amount of crystal C of 2-(3-cyano-4-isobutyloxyphenyl)-4-methyl-5-thiazolecarboxylic acid.

23. A method of producing crystal D of 2-(3-cyano-4-isobutyloxyphenyl)-4-methyl-5-thiazolecarboxylic acid, which comprises crystallizing under the conditions shown as region II in FIG. 1, which are defined by a temperature and a composition of a mixed solvent of methanol and water,
wherein region II is an area surrounded by lines defined by $Y=--0.2X+85$; $Y=1.0X-31$; $Y=20$; and $X=100$,
wherein X is methanol/water composition (U/V %), and Y is temperature (° C.).

24. A method of producing crystal G of 2-(3-cyano-4-isobutyloxyphenyl)-4-methyl-5-thiazolecarboxylic acid, which comprises crystallizing under the conditions shown as region III in FIG. 1, which are defined by a temperature and a composition of a mixed solvent of methanol and water,
wherein region III is an area surrounded by lines defined by $Y=--0.2X+85$; $Y=1.0X-31$; $Y=-3.3X+273$; and $X=50$,
wherein X is methanol/water composition (U/V %), and Y is temperature (° C.).

25. A method of producing crystal G of 2-(3-cyano-4-isobutyloxyphenyl)-4-methyl-5-thiazolecarboxylic acid, which comprises crystallizing from a mixed solvent of 2-propanol and water.

26. A method of producing crystal G of 2-(3-cyano-4-isobutyloxyphenyl)-4-methyl-5-thiazolecarboxylic acid, which comprises air-drying crystal D of 2-(3-cyano-4- isobutyloxyphenyl)-4-methyl-5-thiazolecarboxylic acid under a normal atmosphere.

27. A method of producing an amorphous compound of 2-(3-cyano-4-isobutyloxyphenyl)-4-methyl-5-thiazolecarboxylic acid, which comprises drying crystal D of 2-(3-cyano-4-isobutyloxyphenyl)-4-methyl-5-thiazolecarboxylic acid under a reduced pressure with heating.

* * * * *